United States Patent [19]

Nakane et al.

[11] Patent Number: 5,141,950
[45] Date of Patent: Aug. 25, 1992

[54] BENZIMIDAZOLE COMPOUNDS AND THEIR USE

[75] Inventors: Masami Nakane; Rodney W. Stevens, both of Groton, Conn.

[73] Assignee: Pfizer Inc., New York, N.Y.

[21] Appl. No.: 583,264

[22] Filed: Sep. 14, 1990

[30] Foreign Application Priority Data

Sep. 22, 1989 [JP] Japan .................................. 1-246732

[51] Int. Cl.⁵ .................. A61K 31/415; C07D 235/30; C07D 235/18
[52] U.S. Cl. .................... 514/395; 514/394; 548/329; 548/333; 548/334
[58] Field of Search ....................... 548/329, 333, 334; 514/394, 395

[56] References Cited

U.S. PATENT DOCUMENTS 4,243,806 1/1981 Raeymaekers et al. ............ 544/396
4,835,166 5/1989 Kitaura et al. ..................... 514/339

FOREIGN PATENT DOCUMENTS 209707 1/1987 European Pat. Off. .
312004 4/1989 European Pat. Off. .
8501289 7/1984 World Int. Prop. O. .

OTHER PUBLICATIONS

Hock, C. E. et al., Prostaglandins, 28, 557-570 (1984).
Yoshimoto, T. et al., Biochem. et Biophys. 713, 470-473 (1982).
Chemical Abstracts, vol. 69, No. 65105g Koehler et al.
Chemical Abstracts, vol. 108, No. 5914j. Kuznetsov et al.
Chemical Abstracts, vol. 110, No. 192707v.
Chemical Abstracts, vol. 107, No. 187218v Sakamoto et al.
Chemical Abstracts, vol. 107, No. 124494m Sakamoto et al.
Chemical Abstracts, vol. 107, No. 124477h Sakamoto et al.
Chemical Abstracts, vol. 84, No. 69388j.
Chemical Abstracts, vol. 72, No. 90461q.
Kuzentsov et al., "Derivatives of 5(6)-Aminobenzimidazole" Zh, Org. Khim, 23(3), 637, 1987.
Braeuniger et al., "Preparation of dearza, etc." CA 64:17575a (1966). RN #110208-21-4.

Primary Examiner—Patricia L. Morris
Attorney, Agent, or Firm—Peter C. Richardson; J. Trevor Lumb; Gregg C. Benson

[57] ABSTRACT

Certain benzimidazole compounds and their pharmaceutically acceptable salts, are dual inhibitors of lipoxygenase and cycylooxygenase enzymes, and so are useful as antiallergy and antiinflammatory agents.

16 Claims, No Drawings

BENZIMIDAZOLE COMPOUNDS AND THEIR USE

TECHNICAL FIELD

This invention relates to novel benzimidazole compounds and their use. The new compounds of the present invention are inhibitors of both the cyclooxygenase (CO) and lipoxygenase (LO) enzymes, and are of use in the treatment or alleviation of allergic or inflammatory conditions in mammals including humans.

BACKGROUND OF THE INVENTION

Arachidonic acid is known to be the biological precursor of several groups of endogenous metabolites, prostaglandins including prostacyclins, thromboxanes and leukotrienes. The first step of the arachidonic acid metabolism is the release of esterified arachidonic acid and related unsaturated fatty acids from membrane phospholipids, via the action of phospholipase. Free fatty acids are then metabolized either by cyclooxygenase to produce the prostaglandins and thromboxanes or by lipoxygenase to generate hydroperoxy fatty acids which may be further converted to the leukotrienes. The prostaglandins exhibit diverse physiological effects depending upon their structure. For example, PGE and PGA inhibit gastric secretion as well as lower arterial blood pressure. The thromboxane, especially, thromboxane A2 is a potent vasoconstrictor and platelet aggregatory substance. The leukotrienes are the biological source of the slow reacting substance of anaphylaxis (SRS-A), a chemical mediator in allergic bronchial asthma.

Aspirin and most other non-steroidal antiinflammatory drugs inhibit the cyclooxygenase enzyme. Both antiinflammatory activity and analgesic activity associated inhibition of the action of cyclooxygenase. The lipoxygenase inhibiting activity of one agent, AA861 [2,3,5-trimethyl-6-(12-hydroxy-5,10-cyclodecadiynyl)-1,4benzoquinone], has been reported [see, Yoshimoto el al., Biochem. et Biophys. 713, 470–473 (1982)]. CGS-5391B [(C. E. Hock et al., prostaglandins, 28, 557-571(1984)] has recently become known as a combined cycloxygenase and lipoxygenase inhibitor.

PCT Patent Application PCT/JP84/00452 (WO 85/01289) and Japanese patent publication No. 107958/1988 describe and claim a number of benzoxazolone and benzothiazolone derivatives useful for the treatment of inflammatory conditions and thrombosis.

SUMMARY OF THE INVENTION

The present invention is directed to compounds capable of inhibiting both cyclooxygenase and lipoxygenase. Thus, the present invention provides novel benzimidazole compounds of the formula and their use:

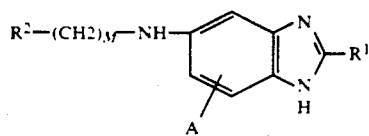

(I)

or a pharmaceutically acceptable salt thereof wherein $R^1$ is H, —NH—$R^3$,

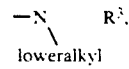

—O$R^3$, —S$R^3$, —alkylene—$R^3$ or $R^4$, $R^3$ is carboxyl, loweralkyl, loweralkoxy, loweralkoxycarbonyl, aryl or heterocyclic, which may be substituted, $R^4$ is aryl or heterocyclic, which may be substituted, $R^2$ is aryl or heterocyclic, which may be substituted, A is H or halo, and m is an integer of 1 to 6.

In the above formula, the term "loweralkyl" means an alkyl group having 1 to 3 carbons. The term "lower alkoxy" and "lower alkoxycarbonyl" mean an alkoxy group and alkoxycarbony group, respectively, having 1 to 5 carbons, preferably up to 2 carbon atoms.

The term "alkylene" means an alkylene group having 1 to 3 carbons. The term "halo" means fluorine, chlorine, bromine or iodine. The term "aryl" means a phenyl group, naphthyl group or cyclohexyl group, and the term "heterocyclic" is one selected from the groups consisting of furyl, pyridyl, pyrimidyl, thiazolyl or thienyl, preferably pyridyl or pyrimidyl.

In the above-mentioned substituents, the aryl group and heterocyclic group may be optionally further substituted by one or more substituents. Preferable substituents are lower alkyl, lower alkoxy and halogen.

The pharmaceutically acceptable salts of the compounds of the formula (I) are those formed from acids which form non-toxic sulfate or bisulfate, phosphate, acetate hydrochloride citrate, fumarate, gluconate, lactate, maleate, succinate, tartrate, methanesulfonate, benzene sulfonate and toluenesulfonate, formate salts.

Among the especially preferred individual compounds of the present invention are:

5-(3-phenylpropyl)amino-2-(o-tolyl) benzimidazole, dihydrochloride;

2-anilino-5-benzylamino benzimidazole, dihydrochloride;

5-benzylamino-2-(3-pyridyl)amino benzimidazole, trihydrochloride;

5-benzylamino-2-propylamino benzimidazole, dihydrochloride;

5-benzylamino-2-(o-toluidino) benzimidazole, dihydrochloride;

5-benzylamino-2-(p-butylanilino) benzimidazole, dihydrochloride;

5-benzylamino-2-(α-naphthyl)amino benzimidazole, dihydrochloride; and

2-[(N-methyl)anilino]-5-benzylamino benzimidazole.

The present invention also includes a pharmaceutical composition comprising a pharmaceutical acceptable carrier or diluent and a compound of formula (I). Also embraced by the present invention is a method for treating an allergic or inflammatory condition in a mammal, especially man.

Also embraced by the present invention is a method of inhibiting the action of the lipoxygenese as well as the action of the cyclooxygenase in a mammal, which comprises administering to such mammal a lipoxygenase and cyclooxygenase inhibiting amount of a compound of formula (I).

DETAILED DESCRIPTION OF THE INVENTION

The compounds of formula (I) may be prepared by a number of different routes. In one embodiment, they are prepared from an amino-substituted compound of the formula (II) according to the following reaction steps:

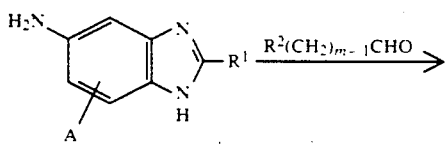

(II)

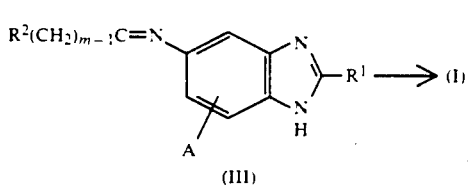

(III)

In the above formulae, $R^1$, $R^2$, m and A are as previously defined. The first step involves the treatment of compound (II) with an aldehyde, $R^2(CH_2)_{m-1}CHO$, in the presence of a dehydrating agent. The reaction is preferably conducted at ambient temperature. Higher temperatures up to 80° C. can be employed without any significant disadvantage. Suitable solvents which do not react with the reactants and/or products are, for example, benzene, toluene, ethanol and tetrahydrofuran. The preferred dehydrating agent is molecular sieves, although inorganic salts such as magnesium sulfate and sodium sulfate can also be employed. When the preferred temperature is used, the reaction is substantially complete within a few hours. On completion, the product (III) can be isolated and/or purified conventionally, e.g. recrystallization or chromatography. It is, however, more convenient not to isolate this product but to subject it (i.e. in situ) to reaction conditions of the second step.

The starting materials (II) and the a)dehyde $R^2(CH_2)_{m-1}CHO$ are either known compounds or may be prepared by methods reported in the art references, see e.g., D. G. Bapat and M. V. Shirsat, Indian J. Chem., 3(2), 81 1965, and J. Garin, E. Melendez, F. L. Merchan, C. Tejel and T. Tejero, Synthtic Commun., 375 1983.

The second step involves reduction of the C=N double bond by reaction with an appropriate hydrogen source. For example, compounds (III) may be reduced catalytically with hydrogen. It is normally achieved with a heterogeneous catalyst such as platinum ($PtO_2$), palladium (Pd/C) or nickel in e.g. methanol or ethanol at ambient temperature. Heating is possible but is not generally necessary.

Alternatively, the compounds may be reduced using a metal hydride. The hydride agents suitably employed in this reduction include sodium borohydride, sodium cyanoborohydride and lithium cyanoborohydride. This reaction is conducted at ambient temperature, with an excess of the hydride agent in e.g methanol or ethanol. A similar reduction using stannous chloride acid agent as a reducing agent can be carried out in methanol-/aqueous hydrochloric acid. A preferred temperature for carrying out this is from 0° C. to 80° C. Reduction is ordinarily complete within a few hours. The product of formula (I) is isolated by standard methods known in the art. Purification can be achieved by conventional means, such as recrystallization or chromatography.

In another embodiment, the compounds of formula (I) are prepared by the following process:

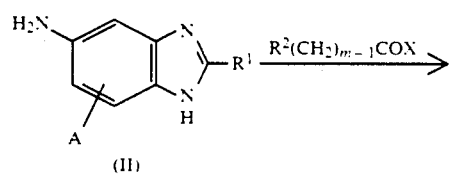

(II)

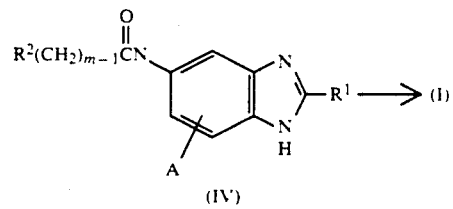

(IV)

In the above formulae, $R^1$, $R^2$, m and A are previously defined and X is a good leaving group.

The amide (IV) is prepared by standard methods known in the art. For example, the amine (II) is reacted with an activated acid (known to those skilled in the art) such as an acid chloride, acid anhydride or activated carboxylic acid (e.g. imidazoyl derivative) in a reaction-inert solvent either in the presence or absence of a base. A wide variety of bases can be used in the reaction and they include organic amines, alkali metal hydroxides, alkaline metal corbonates, alkaline metal hydrocarbonates, alkaline earth metal hydrides and alkaline earth metal alkoxides. Preferred basic agents are triethylamine, pyridine, sodium hydroxide, potassium tert-butoxide, sodium hydride, potassium carbonate and sodium carbonate. Suitable reaction-inert solvents include methylene chloride, tetrahydofuran, benzene, tuluene, xylene and water. The reaction is usually carried out in the temperature range of 0° C. to the boiling point of the solvent. Reaction times of from 30 minutes to a few hours are common. The product can be isolated and purified by conventional procedures, such as recrystallization or chromatography.

The second step usually involves reduction of the amide bond with an appropriate metal hydride. The hydride agents suitably employed in this reduction include lithium aluminum hydride, magnesium aluminum hydride, lithium trimethoxyaluminohydride, sodium bis(2-methoxyethoxy) aluminum hydride, alane and borane preferably in tetrahydrofuran, although ether or dimethoxyethane may be employed. Reaction temperature is usually 0° C. through to reflux. The product of formula (I) is isolated by standard methods and purification can be achieved by conventional means, such as recrystallization or chromatography.

The pharmaceutically acceptable salts of the novel compounds of formula (I) are readily prepared by contacting said compound with a stoichiometric amount of an appropriate mineral or organic acid in either an aqueous solution or a suitable organic solvent. The salt may then be obtained by precipitation or by evaporation of the solvent. Among those salts enumerated earlier, an especially preferred salt is the hydrochloride.

The compounds of formula (I) possess inhibiting activity on the action of the cyclooxygenase as well as on the action of the lipoxygenase. This activity has been demonstrated using rat peritoneal cavity resident cells which determines the effect of said compounds on the metabolism of arachidonic acid.

The ability of the compounds of formula (I) to inhibit both enzymes make them useful for controlling the symptoms induced by the endogenous metabolites arising from arachidonic acid in a mammalian subject. The compounds are therefore valuable in the prevention and treatment of such disease states in which the accumulation of said arachidonic acid metabolite is the causative factor, e.g., allergic bronchial asthma, skin disorders, rheumatoid arthritis, osteoarthritis, and thrombosis.

Since conventional non-steroidal inflammatory agents such as aspirin only inhibit cycloooxygenase, they suppress inflammatory conditions as well as tend to cause adverse inhibition. Compounds of the present invention, however, are gastrointestinally cytoprotective in addition to possessing anti-allergy and anti-inflammatory activities. Thus, they show less adverse effects and are of value for use as a safe drug.

When a compound of the formula (I) or a pharmaceutically acceptable salt thereof is to be used as either an anti-allergic agent or an anti-inflammatory agent, it can be administered to a human subject either alone, or preferably, in combination with pharmaceutically acceptable carriers or diluents in a pharmaceutical composition, in accordance with stand pharmaceutical practice. A compound can be administered by a variety of conventional routes of administration including oral, parental and by inhalation. When the compounds are administered orally, the dose range will be from 0.1 to 20 mg/kg body weight of the subject to be treated per day in single or divided doses. If parental administration is desired, then an effective dose will be from 0.1 to 1.0 mg/kg body weight of the subject to be treated per day. In some instance it may be necessary to use dosages outside these limits, since the dosage will necessarily vary according to the age, weight and response of the individual patient as well as the severity of the patient's symptoms and the potency of the particular compound being administered.

For oral administration, the compounds of formula (I) can be administered, for example, in the form of tablets, powders, lozenges, syrups or capsules, or as an aqueous solution or suspension. In the case of tablets for oral use, carriers which are commonly used include lactose and corn starch, and lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered.

EXAMPLES

The present invention is illustrated by the following examples. However, it should be understood that the examples are simply illustrative and the invention is not limited to the specific details of these examples. Proton nuclear magnetic resonance spectra (NMR) were measured at 270Hz unless otherwise indicated for solutions in perdeuterodimethyl sulfoxide (DMSO-$d_6$) and peak positions are expressed in parts per million (ppm) downfield from tetramethylsilane. The peak shapes are denoted as follows: s, singlet, d, doublet; t, triplet; q, quartet; m, multiplet; b, broad.

EXAMPLE 1

2-Anilino-5-benzylamino benzimidazole dihydrocholoride

5-Amino—2-anilino benzimidazole (4.5 m mol) and benzaldehyde (4.5 m mol) in 15 ml methanol were stirred together for one hour at room temperature. To the reaction mixture was added excess $NaBH_4$ and the reaction mixture stirred a further 30 minutes. The mixture was then concentrated under reduced pressure and resultant residue covered with saturated $NaHCO_3$, extracted into $CH_2Cl_2$ and dried over $Na_2SO_4$. Pure product was isolated by silica gel column chromatography ($CHCl_3$: $CH_3OH$ = 15:1) and the resultant oil covered with $HCl$—$CH_3OH$ and shaken. The resulting dihydrochloride salt was isolated by filtration to afford 2-anilino-5-benzylamino benzimidazole dihydrochloride in 73% yield.

m.p. : >275° C. (dec.)
IR (KBr): 3000(br), 1680 cm$^{-1}$
NMR(DMSO-$d_6$)δ 11.79 (s, 1H), 7.56 – 7.20 (m, 13H) 4.47 (s, 2H)

EXAMPLES

Similarly the following compounds were prepared.

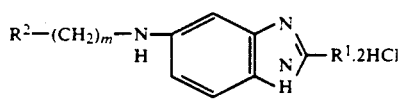

| Example No. | $R^1$ | $R^2$—$(CH_2)_m$— | | IR(KBr) | NMR |
|---|---|---|---|---|---|
| 2. | -NH-C6H4-CH3 | C6H5-CH2- | 268–270° C. decomposed | 2900(br.), 1660 cm$^{-1}$ | 11.69(s, 1H), 7.5–7.1(m, 13H) 4.67(s, 2H), 2.36(s, 3H) |
| 3. | -NH-C6H4-CH3 | C6H5-CH2- | 232–233.5° C. decomposed | 2900(br.), 1670 cm$^{-1}$ | 7.49–7.24(m, 11H), 7.11(br., 1H), 4.44(s, 2H), 2.29(s, 3H) |

EXAMPLES-continued

Similarly the following compounds were prepared.

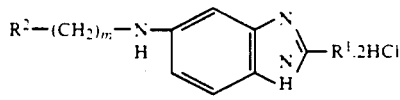

| Example No. | R¹ | R²—(CH₂)ₘ— | m.p. | IR(KBr) | NMR |
|---|---|---|---|---|---|
| 4. | —NH—C₆H₄—CH₃ (para) | —CH₂—C₆H₅ | >270° C. decomposed | 3000(br.), 1700 cm⁻¹ | 7.45–7.25(m, 12H), 6.95(br., 2H), 4.40(s, 2H), 2.35(s, 3H) |
| 5. | —NH—C₆H₄—(CH₂)₃CH₃ | —CH₂—C₆H₅ | >260° C. decomposed | 2900(br.), 1670 cm⁻¹ | 11.35(s, 1H) 7.45–7.43(m, 3H) 7.36–7.27(m, 8H) 7.0(br. 2H) 4.40(s, 2H) 2.61(t, J=7.3Hz, 2H) 1.60–1.55(m, 2H) 1.37–1.29(m, 2H) 0.91(t, J=7.3Hz, 3H) |
| 6. | —NH—(1-naphthyl) | —CH₂—C₆H₅ | >235° C. decomposed | 2800(br.), 1660 cm⁻¹ | 11.71(s, 1H) 8.12–8.02(m, 3H) 7.74–7.59(m, 4H) 7.47–7.07(m, 8H) 4.43(s, 2H) |
| 7. | —NH—(3-pyridyl) (3HCl·0.5H₂O) | —CH₂—C₆H₅ | >270° C. decomposed | 3400, 2700(br.) 1660 cm⁻¹ | 9.29(s, 1H) 8.64–8.56(m, 2H) 8.00–7.94(m, 1H) 7.56–7.28(m, 7H) 7.16(d, J=8.1Hz, 1H) 4.49(s, 2H) |
| 8. | —N(H)—CH₂CH₂CH₃ | —CH₂—C₆H₅ | 205–207° C. | 3200, 2850, 2700 | 12.95(br.s, 2H) 9.23(s, 1H) 7.48(d, J=5.9Hz, 2H) 7.35–7.32(m, 5H) 7.10(d, J=8.8Hz, 1H) 4.46(s, 2H) 3.39–3.31(m, 2H) 1.65–1.57(m, 2H) 0.94(t, J=7.3Hz, 3H) |
| 9. | —N(piperazinyl)N—CH₃ (3HCl·0.5H₂O) | —CH₂—C₆H₅ | <280° C. | 3450, 2600(br.) 1650 cm⁻¹ | 11.74(br.s, 1H) 7.5–7.15(m, 10H) 4.46(s, 2H) 4.46–4.41(m, 2H) 3.86–3.72(m, 2H) 3.65–3.50(m, 2H) 3.36–3.20(m, 2H) 2.78(s, 3H) |
| 10. | —NH—C₆H₄—OCH₃ (meta) | —CH₂—C₆H₅ | 234–237° C. decomposition | 2900, 660 cm⁻¹ | 11.38(s, 1H) 7.45–7.28(m, 7H) 7.02–6.85(m, 5H) 4.40(s, 2H) 3.80(s, 3H) |
| 11. | —N(CH₃)—C₆H₅ (free amine) | —CH₂—C₆H₅ | 73.5–74.6° C. | | 7.28–7.01(m, 12H) 6.48(br.s, 1H) 63.4(dd, J=8.8 and 22Hz, 1H) 4.18(s, 2H) 8.38 s, 3H) |

EXAMPLES-continued

Similarly the following compounds were prepared.

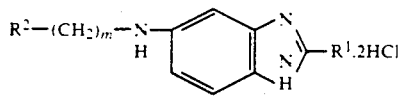

| Example No. | R¹ | R²—(CH₂)ₘ— | | IR(KBr) | NMR |
|---|---|---|---|---|---|
| 12. | —CH₂CH₂COOCH₃ | —CH₂—⌬ | 220.9–224.2° C. | 3500, 2800(br.) 1740 cm⁻¹ | 7.58–7.20(m, 6H) 7.10–6.78(m, 2H) 4.38(s, 2H) 3.60(s, 3H) 3.42–3.22(m, 2H) 3.10–3.00(m, 2H) |
| 13. | —CH₂CH₂COOH (½H₂O) | —CH₂—⌬ | 200.9–202.0° C. | 3200, 2600(br.) 1650 cm⁻¹ | 7.39–7.14(m, 6H) 6.53(d, J=10.3Hz, 1H) 6.45(s, 1H) 5.95(br.s, 1H) 4.27(s, 2H) 2.90(t, J=7.3Hz, 2H) 2.69(t, J=7.3Hz, 2H) |

EXAMPLE 14

5-(3-phenylpropyl) amino-2-phenyl benzimidazole hydrochloride 5-Amino-2-phenyl benzimidazole (19 m mol) and dihydrocinnamoyl chloride (3.12 ml) in 160 ml of benzene were heated at reflux for 3 hours. After cooling the reaction mixture, the resulting precipitate was collected by filtration to afford the hydrochloride salt of the amide in 76% yield.
m.p.: 216.5°–219.5° C.
IR(KBr): 3350, 2800, 1660 cm⁻¹
NMR(DMSO-d₆)δ: 10.45 (s, 1H), 8.41 (s, 1H) 8.35–8.25 (m, 2H), 7.8–7.58 (m, 5H), 7.3–7.19 (m, 5H), 2.96 (6, J=7Hz, 2H) 2.71 (6, J=7Hz, 2H)

To the amide (7m mol) suspended in 50 ml THF was added LiAlH₄ (13 m mol) portionwise in solid form. After addition of all the LiAlH₄, the reaction mixture was heated at reflux for 5 hours, cooled and worked-up by standard procedure. Free alkyl amine was isolated via column chromatography (silica gel, 25% ethyl acetate in hexane) and shaken with HCl-methanol. The dihydrochloride salt was isolated by filtration to afford product in 59% yield.
m.p. : 243.9°–245.9° C.
IR(KBr): 3450, 2700 (br.) cm⁻¹
NMR(DMSO-d₆)δ: 8.37 (br., 2H), 7.73–7.70 (m, 4H) 7.33–7.19(m, 7H), 3.22 (br., 2H) 2.76–2.70(m, 2H), 2.05–1.92 (m, 2H)

EXAMPLES 15–23

Similarly the following compounds were prepared.

| Example No. | R¹ | R²—(CH₂)ₘ— | | IR(KBr) | NMR |
|---|---|---|---|---|---|
| 15. | ⌬—CH₃ | ⌬—(CH₂)₃— | 233–236° C. | 3450, 2700 cm⁻¹ | 7.70–7.49(m, 5H) 7.30–7.19(m, 7H) 3.16(t, J=7.3Hz, 2H) 2.73(t, J=7.3Hz, 2H) 2.56(s, 3H) 2.03–1.90(m, 2H) |
| 16. | ⌬—CH₃ | ⌬—(CH₂)₃— | 245.8–248.1° C. | 2500 cm⁻¹ | 8.25(d, J=8.8Hz, 2H) 7.70(d, J=8.8Hz, 1H) 7.51(d, J=8.1Hz, 2H) 7.32–7.19(m, 7H) 3.20(t, J=8.06Hz, 2H) 2.73(t, J=8.06Hz, 2H) 2.44(s, 3H) 2.01–1.90(m, 2H) |
| 17. | ⌬—CH₃ | ⌬—(CH₂)₃— | >211° C. decomposed | 3400, 2750(br.) cm⁻¹ | 8.23(s, 1H) 8.19(d, J=8.8Hz, 1H) 7.72(d, J=8.8Hz, 1H) 7.64–7.50(m, 2H) 7.40–7.12(m, 7H) 3.21(t, J=8.1Hz, 2H) 2.73(t, J=8.1Hz, 2H) 2.45(s, 3H) 1.99(m, 2H) |

EXAMPLES 15-23-continued

Similarly the following compounds were prepared.

| Example No. | R¹ | R²—(CH₂)ₘ— | | IR(KBr) | NMR |
|---|---|---|---|---|---|
| 18 | cyclohexyl | phenyl-(CH₂)₃— | 241.5-242.7° C. | 3450, 2800(br.) cm⁻¹ | 7.75(d, J=8.8Hz, 1H) 7.58(br. s, 1H) 7.42(d, J=8.8Hz, 1H) 7.32-7.15(m, 5H) 3.25-3.15(m, 3H) 2.71(t, J=6.8Hz, 2H) 2.15-1.66(m, 8H) 1.45-1.20(M, 4H) |
| 19 | 2-pyridyl | phenyl-(CH₂)₃— | 213.1-214.4° C. | 3400, 2650(br.) cm⁻¹ | 8.88(d, J=4.4Hz, 1H) 8.66(d, J=8.1Hz, 1H) 8.2-8.15(m, 1H) 7.76-7.70(m, 2H) 7.45-7.15(m, 7H) 3.21(t, J=6.1Hz, 2H) 2.73(t, J=6.1Hz, 2H) 2.15-1.95(m, 2H) |
| 20 | —(CH₂)₂—phenyl | phenyl-(CH₂)₃— | 270.8-272.8° C. | 2750 cm⁻¹ | 7.7-7.16(m, 13H) 3.44-3.40(m, 2H) 3.25-3.15(m, 4H) 2.70(t, J=7.5Hz, 2H) 2.0-1.9(m, 2H) |
| 21 | —CH₂—phenyl | phenyl-(CH₂)₃— | 243.6-245° C. | 3450, 2800(br.) cm⁻¹ | 7.64(d, J=8.1Hz, 1H) 7.49-7.15(m, 12H) 4.5(s, 2H) 3.20-3.10(m, 2H) 2.70(t, J=8.0Hz, 2H) 2.0-1.9(m, 2H) |
| 22 | 2-fluorophenyl | phenyl-(CH₂)₃— | 240.6-243.3° C. | 2600 (br.) cm⁻¹ | 8.35(t, J=6.0Hz, 1H) 7.78(d, J=8.8Hz, 2H) 7.63-7.45(m, 3H) 7.50-7.15(m, 6H) 3.22(t, J=6.6Hz, 2H) 2.73(t, J=6.6Hz, 2H) 2.18-1.92(m, 2H) |
| 23 | —S—phenyl | phenyl-CH₂— | 200-203° C. | 2800 (br.) cm⁻¹ | 10.3(br., 3H) 7.69-7.12(m, 14H) 4.43(s, 2H) |

We claim:

1. A compound of the formula

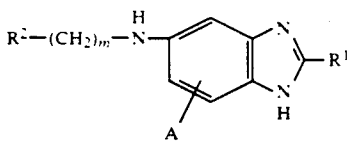

and the pharmaceutically acceptable salts thereof, wherein

R¹ is —NHR³, —NR³(loweralkyl) or R⁴;
R² is phenyl, substituted phenyl, naphthyl or cyclohexyl; wherein the substituents on said substituted phenyl are selected from the group consisting of lower alkyl, lower alkoxy and halo;
R³ is lower alkyl, phenyl, substituted phenyl or naphthyl; wherein the substituents on said substituted phenyl are selected from the group consisting of lower alkyl, lower alkoxy and halo;
R⁴ is phenyl, substituted phenyl, naphthyl or cyclohexyl; wherein the substituents on said substituted phenyl are selected from the group consisting of lower alkyl, lower alkoxy and halo;
A is hydrogen or halo; and
m is an integer of 1 to 3.

2. A compound according to claim 1 wherein
R¹ is phenyl, substituted phenyl or —NH—R³,
R³ is loweralkyl, phenyl, said substituted phenyl or naphthyl;
R⁴ is cyclohexyl,
R² is phenyl,
m is 1-3, and
A is H or halo.

3. A compound according to claim 1 wherein R¹ is

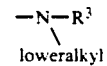

R³ is loweralkyl, phenyl, said substituted phenyl or naphthyl,
R⁴ substituted phenyl
R² is phenyl,
m is 1-3, and
A is H or halo.

4. 5-(3-phenylpropyl) amino-2-(o-tolyl) benzimidazole, dihydrochloride.

5. 2-anilino-5-benzylamino benzimidazole, dihydrochloride.

6. 5-benzylamino-2-propylamino benzimidazole, dihydrochloride.

7. 5-benzylamino-2-(o-toluidino) benzimidazole, dihydrochloride.

8. 5-2-(p-butylanilino) benzimidazole, dihydrochloride.

9. 5-benzylamino-2-(α-naphthyl) amino benzimidazole, dihydrochloride.

10. 2-[N-methyl) anilino] -5-benzylamino benzimidazole.

11. A method of treating an allergic or inflammatory condition which comprises administering to a mammal suffering from an allergic or inflammatory condition an antiallergic or antiinflammatory effective amount of a compound of claim 1.

12. A method of inhibiting the action of lipoxygenase or cyclooxygenase enzymes which comprises administering to a mammal a lipoxygenase or cyclooxygenase inhibiting amount of a compound of claim 1.

13. A compound according to claim 1 wherein $R^3$ is phenyl or said substituted phenyl, $R^2$ is phenyl and m is 1.

14. A compound according to claim 2 wherein $R^3$ is phenyl or said substituted phenyl, $R^2$ is phenyl and m is 1.

15. A compound according to claim 3 wherein $R^3$ is phenyl or said substituted phenyl, $R^2$ is phenyl and m is 1.

16. A pharmaceutical composition suitable for inhibition of cyclooxygenase and lipoxygenase enzymes in a mammalian subject, which comprises a cyclooxygenase or lipoxygenase inhibiting amount of a compound according to claim 11 and a pharmaceutically acceptable carrier or diluent.

* * * * *